(12) United States Patent
Bolam

(10) Patent No.: US 7,287,391 B2
(45) Date of Patent: *Oct. 30, 2007

(54) AUTOMATED MODULAR HYPERPOLARIZERS AND RELATED DEVICES AND METHODS

(75) Inventor: Kenneth Bolam, Raleigh, NC (US)

(73) Assignee: Medi-Physics, Inc., Princeton, NJ (US)

( * ) Notice: Subject to any disclaimer, the term of this patent is extended or adjusted under 35 U.S.C. 154(b) by 561 days.

This patent is subject to a terminal disclaimer.

(21) Appl. No.: 10/277,911

(22) Filed: Oct. 22, 2002

(65) Prior Publication Data

US 2003/0108485 A1    Jun. 12, 2003

(51) Int. Cl.
```
B01D 8/00      (2006.01)
F25B 21/00     (2006.01)
F25B 49/00     (2006.01)
G01N 1/00      (2006.01)
G01N 24/00     (2006.01)
```
(52) U.S. Cl. .......................... 62/55.5; 62/3.1; 62/132; 422/22; 436/173; 436/8; 436/149; 436/174; 436/181

(58) Field of Classification Search ................ 436/173, 436/8, 149, 174, 181; 62/3.1, 55.5, 132; 422/22

See application file for complete search history.

(56) References Cited

U.S. PATENT DOCUMENTS

| | | | |
|---|---|---|---|
| 5,545,396 A | 8/1996 | Albert et al. | 424/93 |
| 5,642,625 A | 7/1997 | Cates, Jr. et al. | 62/55.5 |
| 5,809,801 A | 9/1998 | Cates, Jr. et al. | 62/637 |
| 6,079,213 A | 6/2000 | Driehuys et al. | 62/3.1 |
| 6,286,319 B1 * | 9/2001 | Hasson et al. | 62/49.1 |
| 6,295,834 B1 | 10/2001 | Driehuys | 62/637 |
| 6,523,356 B2 * | 2/2003 | Hasson et al. | 62/49.1 |
| 6,566,875 B1 * | 5/2003 | Hasson et al. | 324/309 |
| 6,630,126 B2 * | 10/2003 | Driehuys et al. | 424/9.3 |
| 2001/0029739 A1 | 10/2001 | Zollinger | 62/3.1 |
| 2002/0029586 A1 * | 3/2002 | Driehuys | 62/637 |
| 2003/0109058 A1 * | 6/2003 | Bolam | 436/173 |

OTHER PUBLICATIONS

Rosen M S. etal. "Polarized 129XE Optical Pumping/Spin Exchange and Delivery System for Magnetic Resonance Spectroscopy and Imaging Studines" Review of Scientific Instruments, American Institute of Physics, New York, US vol. 70, No. 2 Feb. 1999, pp. pp. 1546-1552 xp0008796078.

Saam, et.al. "Low Frequencey NMR Polarimeter for Hyperpolarized Gases" Journal of Magnetic Resonance 134, pp. 67-71 (1998).

* cited by examiner

Primary Examiner—Brian Sines
(74) Attorney, Agent, or Firm—Robert F. Chisholm

(57) ABSTRACT

Modular expandable hyperpolarizers include a central control module and at least one optical pumping module that can be expandable to a plurality of optical pumping modules that can be separately operated depending on the capacity demands at the production site (hospital, clinic and the like). Methods for producing blended polarized gas products include introducing a pre-packaged pre-mixed amount of a polarizer-ready blend of unpolarized gas. Methods for producing the polarized gas can be carried out at the point of use site and the production run according to patient load. Other methods consider the patient load and automatically schedule the hyperpolarizer to yield the desired polarized gas doses to support the patient and/or MRI/NMR equipment schedule.

20 Claims, 10 Drawing Sheets

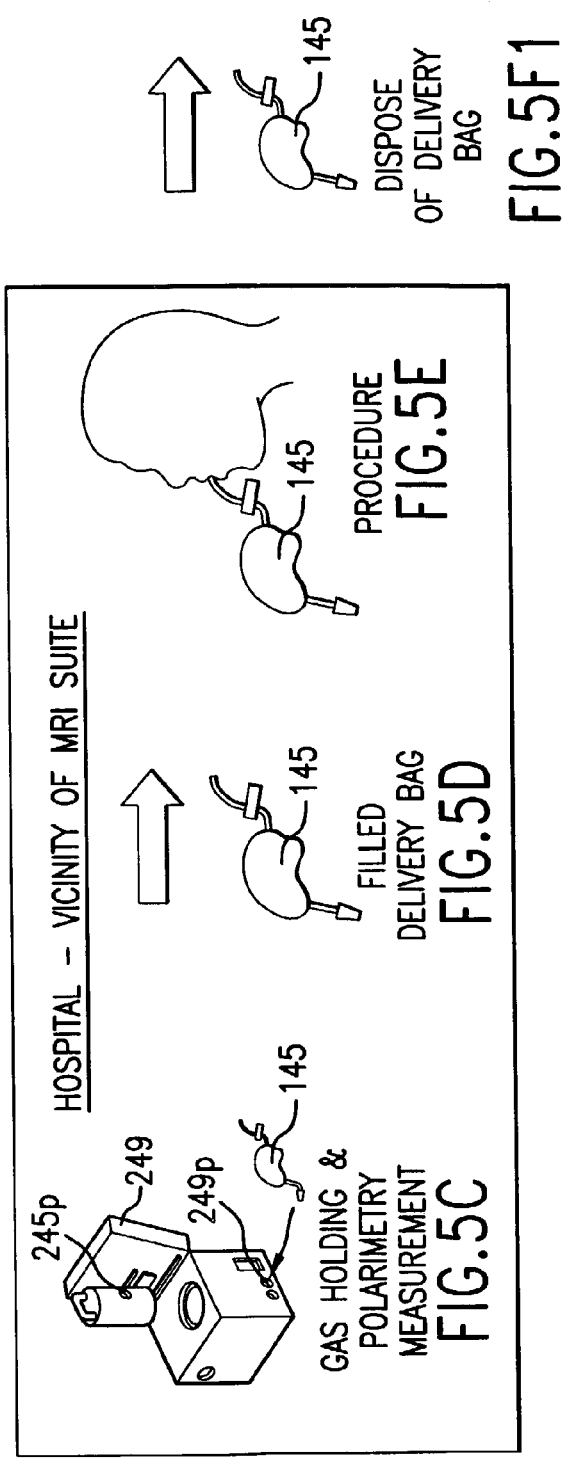
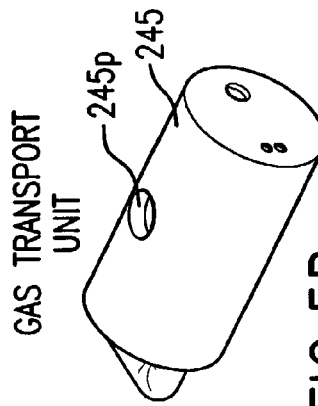
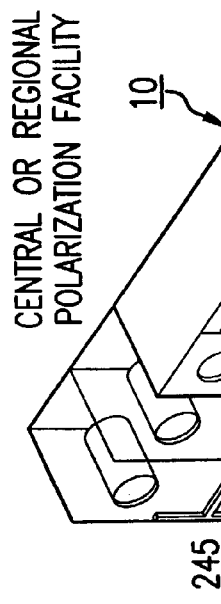
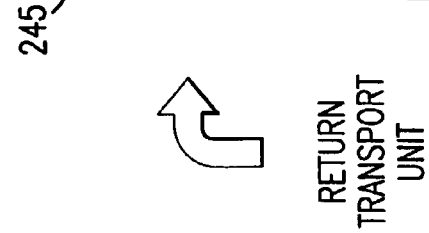

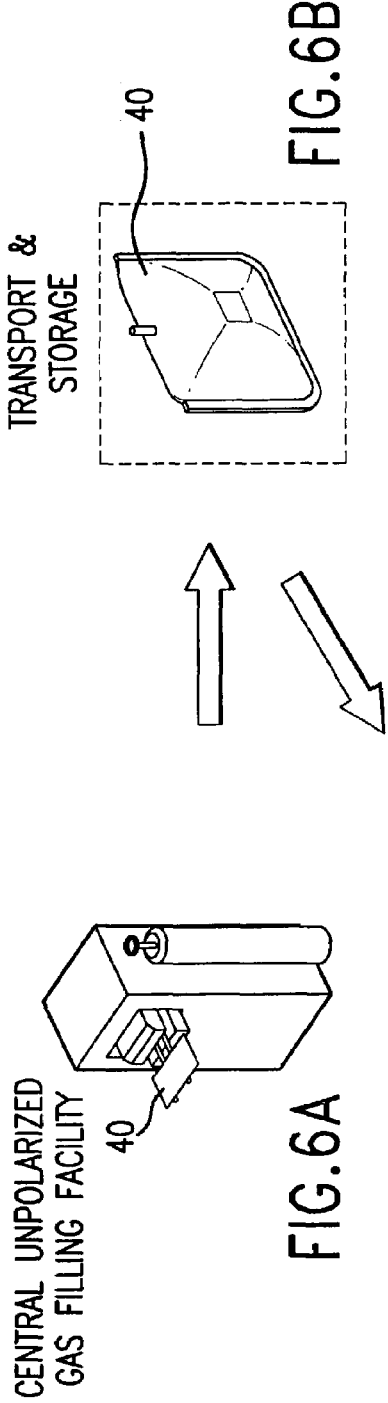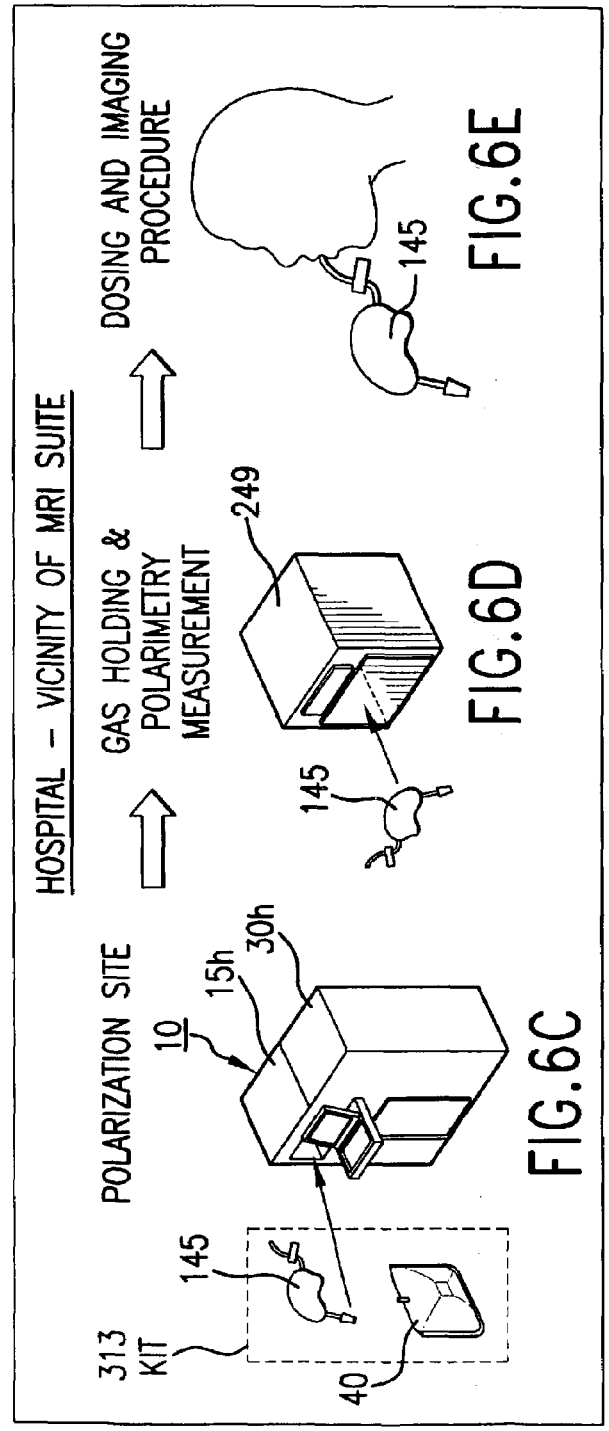

AUTOMATED MODULAR HYPERPOLARIZERS AND RELATED DEVICES AND METHODS

FIELD OF THE INVENTION

The present invention relates to the production of polarized noble gases used in NMR and magnetic resonance imaging ("MRI") applications.

BACKGROUND OF THE INVENTION

It has been discovered that polarized inert noble gases can produce improved MRI images of certain areas and regions of the body that have heretofore produced less than satisfactory images in this modality. Polarized helium-3 ("$^3$He") and xenon-129 ("$^{129}$Xe") have been found to be particularly suited for this purpose. Unfortunately, as will be discussed further below, the polarized state of the gases is sensitive to handling and environmental conditions and can, undesirably, decay from the polarized state relatively quickly.

Hyperpolarizers are used to produce and accumulate polarized noble gases. Hyperpolarizes artificially enhance the polarization of certain noble gas nuclei (such as $^{129}$Xe or $^3$He) over the natural or equilibrium levels, i.e., the Boltzmann polarization. Such an increase is desirable because it enhances and increases the MRI signal intensity, allowing physicians to obtain better images of the substance in the body. See U.S. Pat. Nos. 5,545,396; 5,642,625; 5,809,801; 6,079,213, and 6,295,834; the disclosures of these patents are hereby incorporated by reference herein as if recited in full herein.

In order to produce the hyperpolarized gas, the noble gas is typically blended with optically pumped alkali metal vapors such as rubidium ("Rb"). These optically pumped metal vapors collide with the nuclei of the noble gas and hyperpolarize the noble gas through a phenomenon known as "spin-exchange." The "optical pumping" of the alkali metal vapor is produced by irradiating the alkali-metal vapor with circularly polarized light at the wavelength of the first principal resonance for the alkali metal (e.g., 795 nm for Rb). Generally stated, the ground state atoms become excited, then subsequently decay back to the ground state. Under a modest magnetic field (10 Gauss), the cycling of atoms between the ground and excited states can yield nearly 100% polarization of the atoms in a few microseconds. This polarization is generally carried by the lone valence electron characteristics of the alkali metal. In the presence of non-zero nuclear spin noble gases, the alkali-metal vapor atoms can collide with the noble gas atoms in a manner in which the polarization of the valence electrons is transferred to the noble-gas nuclei through a mutual spin flip "spin-exchange."

Generally stated, as noted above, conventional hyperpolarizers include an optical pumping chamber held in an oven and in communication with a laser source that is configured and oriented to transmit circularly polarized light into the optical pumping chamber during operation. The hyperpolarizers may also monitor the polarization level achieved at the polarization transfer process point, i.e., at the optical cell or optical pumping chamber. In order to do so, typically a small "surface" NMR coil is positioned adjacent the optical pumping chamber to excite and detect the gas therein and thus monitor the level of polarization of the gas during the polarization-transfer process. See U.S. Pat. No. 6,295,834 for further description of polarization monitoring systems for optical pumping cells and polarizers.

In any event, it is now known that on-board hyperpolarizer monitoring equipment no longer requires high-field NMR equipment, but instead can use low-field detection techniques to perform polarization monitoring for the optical cell at much lower field strengths (e.g., 1-100 G) than conventional high-field NMR techniques. This lower field strength allows correspondingly lower detection equipment operating frequencies, such as 1-400 kHz. More recently, Saam et al. has proposed a low-frequency NMR circuit expressly for the on-board detection of polarization levels for hyperpolarized $^3$He at the optical chamber or cell inside the temperature-regulated oven that encloses the cell. See Saam et al., *Low Frequency NMR Polarimeter for Hyperpolarized Gases*, Jnl. of Magnetic Resonance 134, 67-71 (1998). Others have used low-field NMR apparatus for on-board polarization measurement.

After the spin-exchange has been completed, the hyperpolarized gas is typically separated from the alkali metal prior to introduction into a patient (to form a non-toxic pharmaceutically acceptable product). Unfortunately, both during and after collection, the hyperpolarized gas can deteriorate or decay relatively quickly (lose its hyperpolarized state) and therefore must be handled, collected, transported, and stored carefully. Thus, handling of the hyperpolarized gases is critical, because of the sensitivity of the hyperpolarized state to environmental and handling factors and the potential for undesirable decay of the gas from its hyperpolarized state.

As demand for the polarized gas increases, there is a need for methods and systems that can provide increased volume production of the polarized gas to meet production demands in a manner that provides a reliable supply of polarized gas in a relatively economic manner that can consider and facilitate hospital or clinical scheduling of associated equipment (MRI or NMR systems).

OBJECTS AND SUMMARY OF THE INVENTION

In view of the foregoing, it is an object of the present invention to provide hyperpolarizers, systems, methods, and computer program products to provide increased timely production of polarized gases.

It is an additional object of the present invention to provide an automated hyperpolarizer that can operate multiple optical pumping modules that can produce increased amounts of polarized gases either serially or in parallel.

It is another object of the present invention to provide a hyperpolarizer system and associated production kits that are configured to be operated at the point-of-use.

It is yet another object of the present invention to provide kits of unpolarized gas mixtures that can be accepted into the hyperpolarizer and provide polarized gas products in a controlled manner so as to meet regulatory guidelines.

These and other objects are satisfied by the present invention by at least one of the distribution system and/or hyperpolarizer apparatus that includes a control module and a plurality of modular optical pumping cells and other related support kits and devices.

Certain embodiments of the present invention are directed to hyperpolarizers for producing polarized noble gases. The hyperpolarizers include: (a) a control module configured to direct the operation of the hyperpolarizer; (b) a first optical pumping module operably associated with the control module; (c) a second optical pumping module operably associated with the control module; and (d) a scheduling sequencer unit comprising program code for accepting user input regarding polarized gas requirements and program code for automatically scheduling the operation of at least one of the first and second optical pumping modules based on the polarized gas requirements.

The first and second optical pumping modules may be configured such that, during operation, they are in concurrent communication with the control module so that the control module can direct the first and second optical pumping modules to commence operation either serially so that the start times are sequentially staggered in time or so that operation does not overlap or in parallel so that the operate concurrently for at least a portion of the time based on the production requirements.

The hyperpolarizer may include upgrade capacity so that it supports three, four, or more optical pumping modules concurrently.

Other embodiments are directed to production capacity expandable hyperpolarizers. The hyperpolarizers comprise a control module and a plurality of expansion slots, each expansion slot configured to engage the control module with an optical pumping module, wherein the hyperpolarizer can operate both with one optical pumping module and a plurality of optical pumping modules depending on a production site's capacity requirements.

The expansion slots may be gas independent (i.e., work with either $^{129}$Xe or $^{3}$He).

Other embodiments are directed to kits for producing polarized noble gas. The kit can include: (a) a sealed container comprising a predetermined quantity of a pharmaceutical grade unpolarized gas mixture comprising an inert noble gas to be polarized and a second high-purity carrier gas therein; and (b) a dispensing container configured to hold a quantity of polarized gas mixture therein.

Still other embodiments of the present invention are directed to methods of providing polarized noble gas for NMR or MRI applications. The methods include: (a) delivering a pre-packaged quantity of unpolarized gas mixture comprising a noble gas to be polarized to a point of use site; (b) expelling the unpolarized gas mixture from the package into a hyperpolarizer located at the point of use; (c) polarizing the noble gas via spin-exchange interactions with an alkali metal in the hyperpolarizer; (d) measuring the polarization level of the noble gas; (e) dispensing the polarized noble gas out of the hyperpolarizer into a patient dispensing device; and (f) blending in situ at the point of use site, the polarized noble gas with a biocompatible fluid to provide a pharmaceutical grade polarized noble gas product suitable for in vivo administration to a subject.

Other embodiments are directed to methods for supplying meted amounts of unpolarized pharmaceutical grade inert noble gas mixtures, each formulated to be independently introduced to a hyperpolarizer to provide polarized noble gas. The method includes: (a) introducing a meted single batch quantity of an unpolarized pharmaceutical grade noble gas mixture into a container at a production site, the meted batch quantity comprising a predetermined amount of carrier gas and a predetermined amount of inert noble gas, the single batch quantity being sufficient to yield polarized gas in a quantity sufficient for a single patient during a single MRI or NMR evaluation session; and (b) sealing the container so that the unpolarized pharmaceutical grade noble gas mixture has a shelf life of at least about 1-6 months.

An additional embodiment is a method of polarizing unpolarized inert noble gas in a hyperpolarizer, comprising: (a) receiving a plurality of pre-packaged containers of predetermined quantities of an unpolarized gas mixture, the unpolarized gas mixture comprising a noble inert gas and a carrier gas; (b) engaging one of the pre-packaged containers of the unpolarized gas mixture to a hyperpolarizer having an optical pumping cell and an unpolarized gas inlet path and a polarized gas exit path; (c) releasing the unpolarized gas mixture from the pre-packaged container; (d) directing the unpolarized gas mixture to travel to through the gas inlet path to the optical pumping cell; (e) polarizing the gas via spin-exchange interactions with an alkali metal held in the optical pumping cell; (i) heating the optical pumping cell during the polarizing step; (g) cooling the polarized gas; (h) measuring the polarization level of the polarized gas; (i) dispensing the polarized gas from the optical pumping cell and out of the gas exit path; and (6) blending $N_2$ with the dispensed polarized gas to provide a pharmaceutical grade polarized gas formulation. In particular embodiments, the method can be carried out at a point of use site.

Still other embodiments are directed to methods of operating a hyperpolarizer having a plurality of optical pumping cells. The method includes: (a) identifying the polarized gas requirements for a selected time period based on patient scheduling; and (b) automatically determining a production operation sequence schedule of the hyperpolarizer so as to identify the start times of each of the plurality of optical pumping cells and the number of batches to be produced by each of the optical pumping cells so as to be able to produce polarized gas in a sufficient quantity to meet the identified polarized gas requirements.

Additional embodiments of the invention are directed to computer program products for operating a hyperpolarizer having at least one optical pumping cell to produce polarized noble gas. The computer program product comprises a computer readable storage medium having computer readable program code embodied in the medium, the computer-readable program code comprises: (a) computer readable program code that determines the desired polarized gas production goals over a selected time; (b) computer readable program code that schedules the sequence of activation and start times of the polarization process in the optical pumping cells; and (c) computer readable program code that automatically initiates the operation of at least one of the optical pumping cells according to the scheduled sequence.

In particular embodiments, the computer program product can also include program code that accepts user input regarding patient scheduled appointments where polarized gas is needed and the computer readable program code that schedules the sequence of activation and start times of the polarization process in the optical pumping cells considers the patient schedule demands for polarized gas.

Advantageously, the present invention can provide increased timely production of hyperpolarized gas where patient-sized quantities (such as 0.5-2 liters of polarized gas) can be produced to support to the clinic or hospital.

The foregoing and other objects and aspects of the present invention are explained in detail herein.

BRIEF DESCRIPTION OF THE DRAWINGS

FIG. 5 is a schematic illustration of a central or regional polarized gas distribution model according to embodiments of the present invention. FIG. 5A-5E illustrate steps associated therewith and FIGS. 5F1 and 5F2 illustrate post-use steps according to embodiments of the present invention.

FIG. 6 is a schematic illustration of point of use (hospital or clinical facility or portable system positioned) with the hyperpolarizer positioned proximate an MRI suite. FIGS. 6A-6E illustrate steps associated therewith while FIG. 6F illustrates a post processing step.

DETAILED DESCRIPTION OF EMBODIMENTS OF THE INVENTION

Figure 1A:
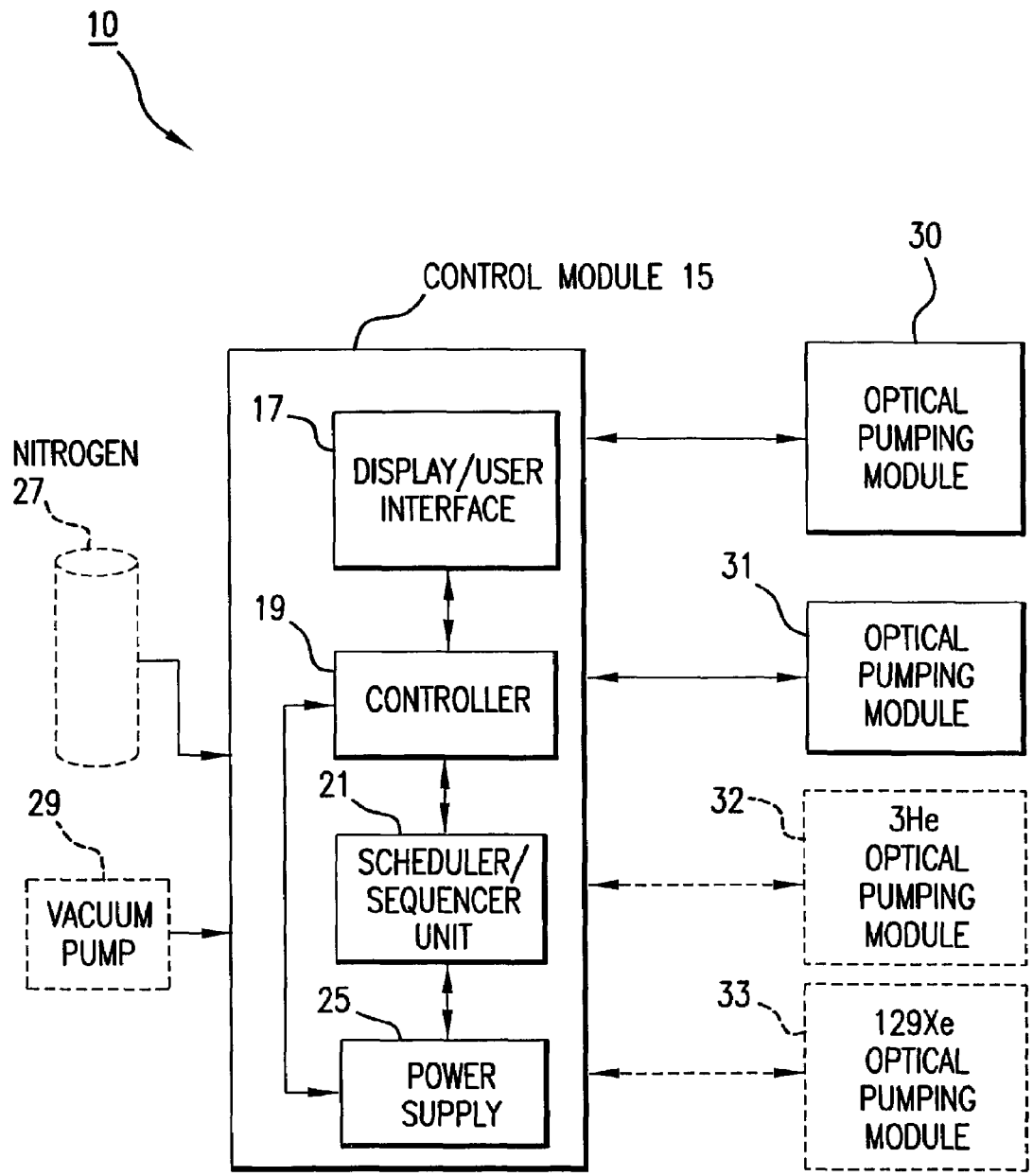
FIG. 1A is a block diagram of a hyperpolarizer with a control module and a plurality of optical pumping modules according to embodiments of the present invention.

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. In the drawings, layers, regions, or components may be exaggerated for clarity. In the figures, broken lines in the flow charts indicate optional features.

In the description of the present invention that follows, certain terms may be employed to refer to the positional relationship of certain structures relative to other structures. As used herein the term "forward" and derivatives thereof refer to the general direction the gas mixture travels as it moves through the hyperpolarizer unit; this term is meant to be synonymous with the term "downstream," which is often used in manufacturing environments to indicate that certain material being acted upon is farther along in the manufacturing process than other material. Conversely, the terms "rearward" and "upstream" and derivatives thereof refer to the directions opposite, respectively, the forward and downstream directions.

Also, as described herein, polarized gases are collected and may, in particular embodiments, be frozen, thawed, and then used in MRI or NMR spectroscopy applications. For ease of description, the term "frozen polarized gas" means that the polarized gas has been frozen into a solid state. The term "liquid polarized gas" means that the polarized gas has been or is being liquefied into a liquid state. Thus, although each term includes the word "gas," this word is used to name and descriptively track the gas that is produced via a hyperpolarizer to obtain a polarized "gas" product. Thus, as used herein, the term "gas" has been used in certain places to descriptively indicate a hyperpolarized noble gas product and may be used with modifiers such as solid, frozen, and liquid to describe the state or phase of that product. The polarized gas product may include other constituents such as other carrier gases or carrier liquids as desired.

Various techniques have been employed to accumulate and capture polarized gases. For example, U.S. Pat. No. 5,642,625 to Cates et al. describes a high volume hyperpolarizer for spin-exchange polarized noble gas and U.S. Pat. No. 5,809,801 to Cates et al. describes a cryogenic accumulator for spin-polarized $^{129}$Xe. As used herein, the terms "hyperpolarize," "polarize," and the like, are used interchangeably and mean to artificially enhance the polarization of certain noble gas nuclei over the natural or equilibrium levels. Such an increase is desirable because it allows stronger imaging signals corresponding to better MRI images of the substance and a targeted area of the body. As is known by those of skill in the art, hyperpolarization can be induced by spin-exchange with an optically pumped alkali-metal vapor or alternatively by metastability exchange. See Albert et al., U.S. Pat. No. 5,545,396.

The present invention is described in certain portions of the specification with reference to flowchart illustrations and/or block diagrams of methods, and computer program products according to certain embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, embedded processor or other programmable data processing apparatus to produce a machine, such that the instructions, which execute via the processor of the computer or other programmable data processing apparatus, create means for implementing the functions specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

As will be appreciated by one of skill in the art, the present invention may be embodied as a method, data or signal processing system, computer program product, and may include certain electromechanical or hardware components. Accordingly, certain embodiments of the present invention may take the form of an entirely software embodiment or an embodiment combining software and hardware aspects. Furthermore, the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java7, Smalltalk or C++. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user=s computer and partly on a remote computer or entirely on the remote computer. In the latter scenario, the remote computer may be connected to the user=s computer through a local area network (LAN) or a wide area network (WAN), or the connection may be made to an external computer (for example, through the Internet using an Internet Service Provider).

Certain of the flowcharts and block diagrams illustrate methods to operate hyperpolarizers or components thereof to yield polarized gas according to embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

Referring to FIG. 1A, this block diagram illustrates one embodiment of a modular hyperpolarizer 10. As shown, the,primary modules include a control module 15 and a plurality of optical pumping modules 30, 31 with two more optical pumping modules 32, 33 optionally available. The plurality of optical pumping modules can be provided in any suitable quantity, such as two, three, four or more. As such, the hyperpolarizer 10 can be configured to operate with one or more optical pumping modules and still have the capacity to add additional modules as production demands increase. Alternatively, the hyperpolarizer 10 can be manufactured with all available optical pumping module spaces filled. This modular configuration and operation can allow for site customization (to meet a particular production site's capacity requirements). In addition, field repairs may be improved by using modular replacement parts.

Figure 1B:
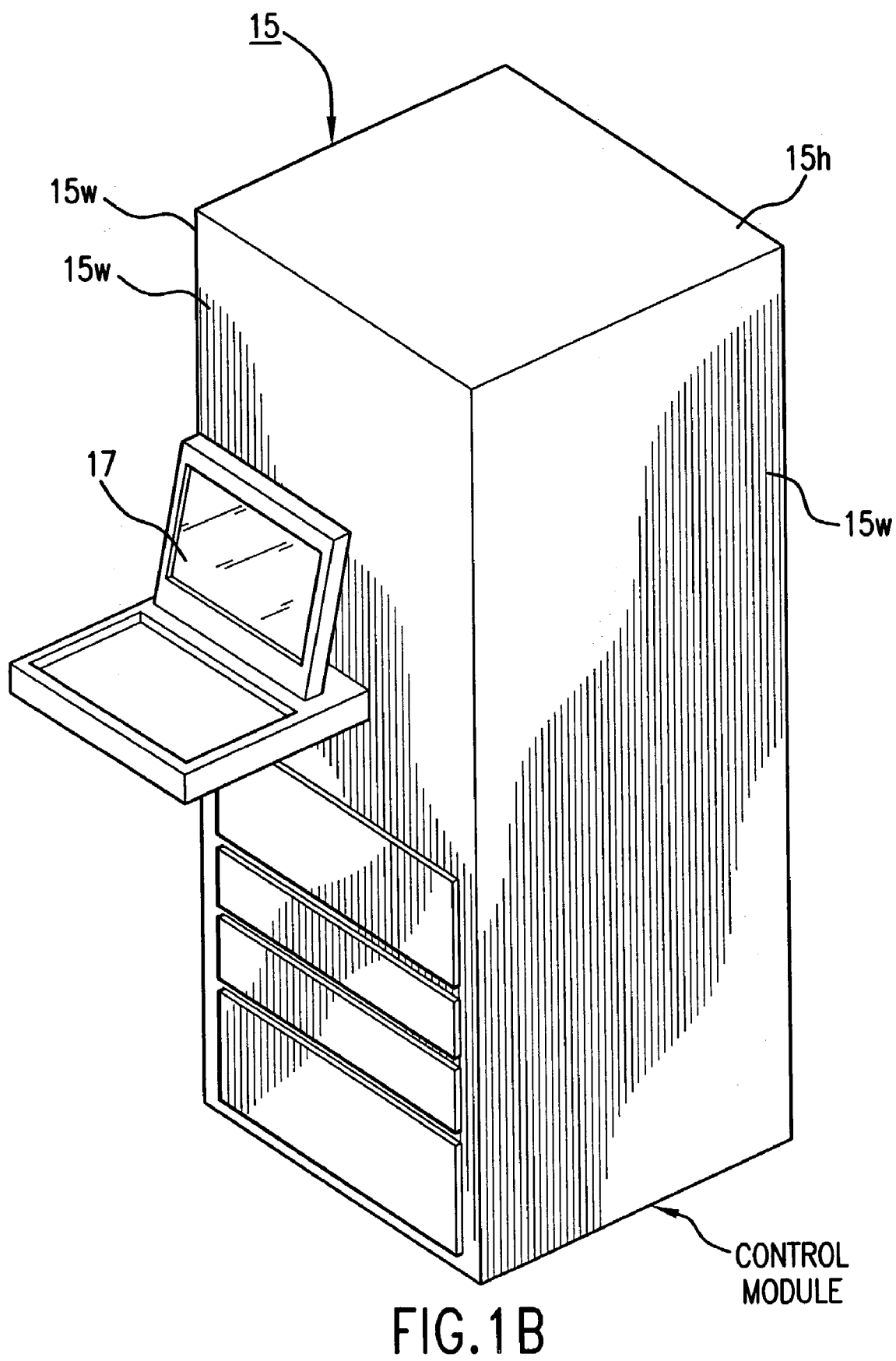
FIG. 1B is a perspective view of a control module for a hyperpolarizer according to embodiments of the present invention.

The hyperpolarizer 10 also includes a source of high purity purge gas 27 (such as grade 5 Nitrogen) and a vacuum pump 29. As shown, the purge gas 27 and vacuum pump 29 are configured to engage with the control module 15. As shown in FIG. 1B, the control module 15 can be held in a housing 15$h$ with upstanding sidewalls 15$w$. At least one of the sidewalls 15$w$ can be configured to provide access to the operational (electrical and mechanical) mating components 15$c$ (FIG. 1C) between the optical pumping modules and the control module to allow fluid or electrical control attachments for one or more of: air (compressed) or hydraulic fluid for automated controls; and fluid for exchange via the gas/purge plumbing; and electrical connections. The control module housing 15$h$ can be configured to have a reduced footprint to reduce the space demand to support the equipment in the production environment or facility.

As shown in FIG. 1A, the control module 15 also includes a display/user interface 17, a controller 19 that controls the operation of the hyperpolarizer 10, a scheduler/sequencer unit 21, and a power supply 25.

The display and/or user interface or input means 17 can include a monitor as well as a keyboard or touch screen or the like that can allow an operator to input patient scheduling information to allow the hyperpolarizer 10 to determine or forecast a desired production operation schedule to meet the patient use demands. In other embodiments, the user interface can be configured to allow remote input of the scheduling via a computer network, whether, local, regional, national (intranet) or global (internet). The display or interface 17 can also display or relay information regarding the operational status and function of the hyperpolarizer 10 such as the polarization level of the gas in the optical pumping module(s) 30, 31 or any detected operational errors or discrepancies during operation.

Figure 1C:
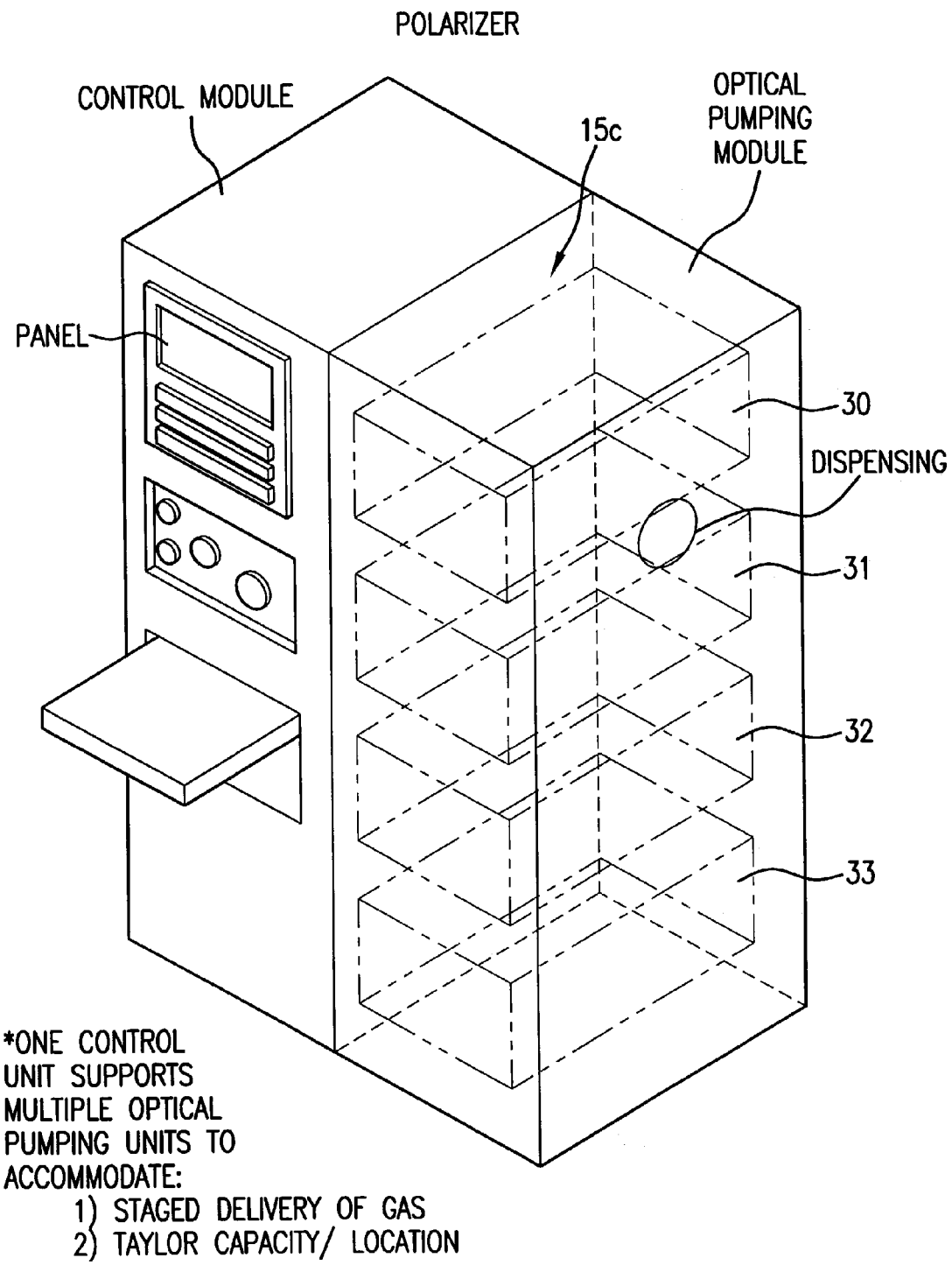
FIG. 1C is a perspective view of a hyperpolarizer with a control module and a plurality of optical pumping modules according to embodiments of the present invention.

As also shown in FIG. 1A, the optical pumping modules may be either as all $^3$He modules, all $^{129}$Xe modules, or a combination of desired numbers of both $^3$He and $^{129}$Xe modules (such as two $^3$He, and one $^{129}$Xe). In particular embodiments, the station can be configured to accept either $^3$He or $^{129}$Xe in a particular slot, depending on a site's production needs. FIG. 1C illustrates that the hyperpolarizer 10 can include side-by-side matable housings: one for the control module 15$h$, and one for the optical pumping modules 30$h$. The optical pumping modules 30, 31 (that may include additional modules 32, 33) can be arranged to be vertically stacked in alignment or to be positioned side by side, or on opposing sides of the control module 15$h$ (not shown). The vertically stacked arrangement can reduce the foot print space requirement for the equipment at the production facility. The optical pumping modules 30, 31 may be configured to slide into cavities or shelves formed in the housing 30$h$ (not shown) (so as to position the modules to be spaced apart a distance), or may be configured as self-stacking units or pairs of units so that two or more of the modules 30, 31 (and/or 32, 33) contact each other when in position.

As will be understood by those of skill in the art, in certain embodiments, the control module 15 is configured to provide the purge/pump capacity from a central purge gas source 27 and vacuum pump 29 to each of the optical pumping modules 30, 31. As such, fluid flow paths of plumbing extending between the purge and vacuum sources to each of the optical pumping modules are defined by a fluid distribution system or manifold network of plumbing, valves, and solenoids. These fluid flow paths selectively direct purge gas to and from the optical pumping cells 30, 31 to purge and evacuate the optical pumping modules and related flow paths in order to prepare them for polarization operation.

Figure 2:
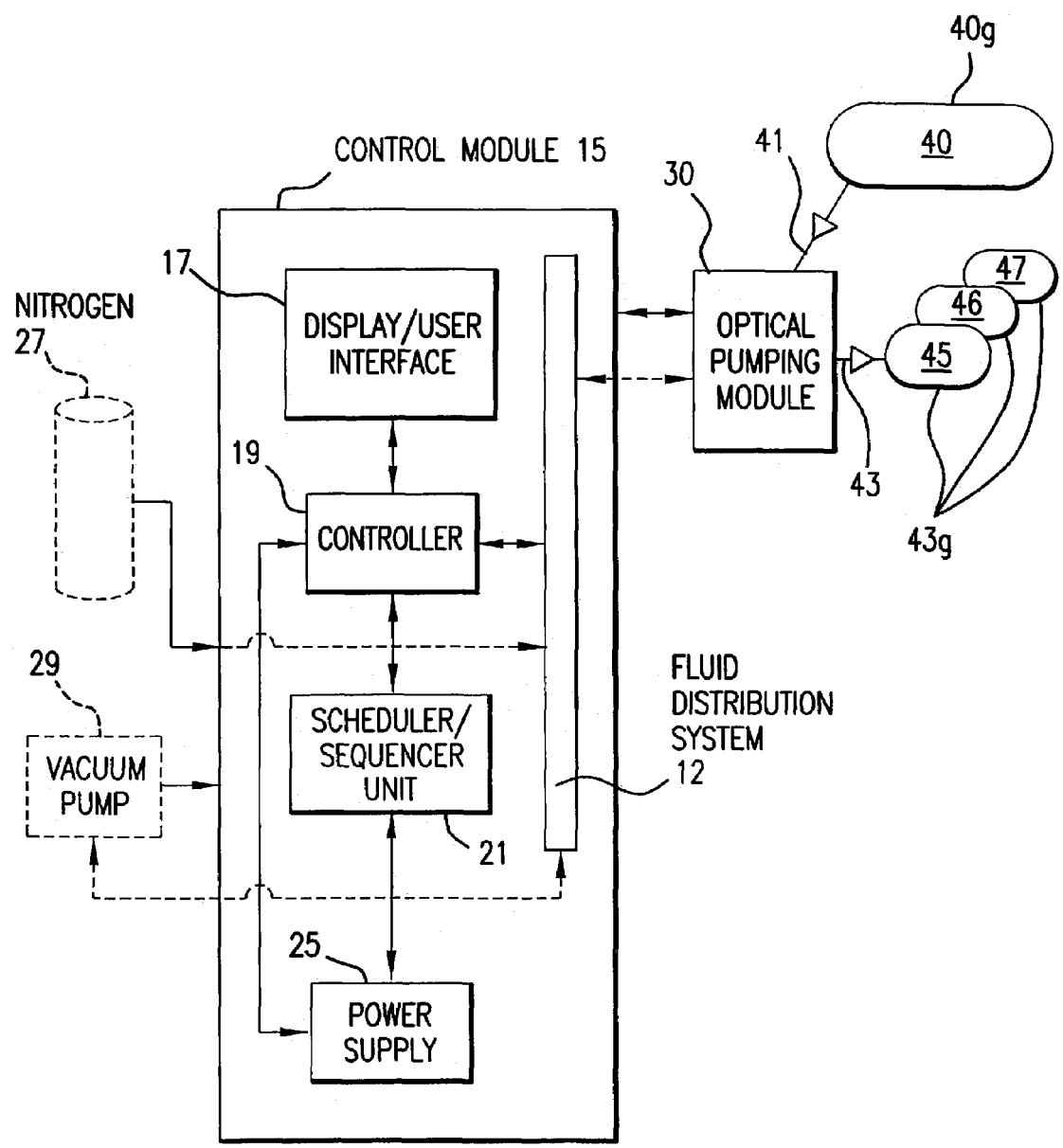
FIG. 2 is a block diagram of a control module and an optical pumping module according to embodiments of the present invention.

FIG. 2 illustrates the control module 15 with a fluid distribution system 12 that is in fluid communication with the purge gas source 27 and the vacuum pump 29 (shown by the broken line between these components and the fluid distribution system 12) and that is operably associated with the controller 19. The fluid distribution system 12 is also in fluid communication with the optical pumping module 30 (and the other modules that may be attached to or connected with the control module 15), as is also indicated by the broken line therebetween in the figure.

Generally stated, the scheduler/sequencer unit 21 determines the appropriate operational sequence and production run schedule(s) of one or more of the optical pumping cells to meet user requirements (recognizing that there is a limited life to the polarized gas and, hence a limited shelf life). The controller 19 initiates the pump/purge preparation process proximate in time to the desired production operation schedule to clean and prepare the optical pumping cell and associated plumbing for receiving an unpolarized quantity of noble gas mixture and to begin the spin-exchange polarization process each time an optical module is scheduled for a production run.

As shown in FIG. 2, a quantity of pre-packaged unpolarized gas mixture in a container 40 is received at a gas access (inlet) port 41 on the optical pumping module 30. The quantity can be sized so as to provide the constituents commensurate with that needed to form a single batch. Typically, the pre-packaged unpolarized gas mixture comprises a minor amount of the target noble gas and a larger quantity of one or more high purity biocompatible filler gases. For example, for $^3$He polarization, an unpolarized gas blend of $^3$He/N$_2$ can be about 99.25/0.75. For producing hyperpolarized $^{129}$Xe, the pre-mixed unpolarized gas mixture can be about 85-98% He (preferably about 85-89% He), about 5% or less $^{129}$Xe, and about 1-10% N$_2$ (preferably about 6-10%).

The pre-packaged amount of unpolarized gas mixture in the container (and the optical cell itself) can be meted out and configured and sized so that the single batch production run quantity provides a single patient amount for a single MRI imaging or NMR evaluation session. To provide the pharmaceutical grade polarized gas doses, the polarized gas itself may be mixed with pharmaceutical grade carrier gases or liquids, or may be configured to be administered as the only or primary substance or constituent. In particular embodiments, the polarized gas is $^3$He and is mixed with nitrogen filler gas to form a volume of gas blend to be inhaled by the patient. In other embodiments, for example, for producing inhalable $^{129}$Xe, the $^{129}$Xe may form a major portion (or all) of the administered dose. In other embodiments, the polarized gas can be formulated to be injected in vivo (in a liquid carrier, in microbubble solution, or in gaseous form).

In any event, as illustrated in FIG. 2 by the plurality of receiving containers 45, 46, 47, attached to a polarized gas exit port 43 of the optical pumping module 30, the volume of polarized gas produced per batch can be sufficient to provide polarized gas or polarized gas blend in sufficient amounts to yield a plurality of separate (inhalable) boluses administered to the subject over a single NMR or MRI session. Although shown as separate features, the polarized gas exit port 43 may be the same port as the inlet port 41.

Figure 3A:
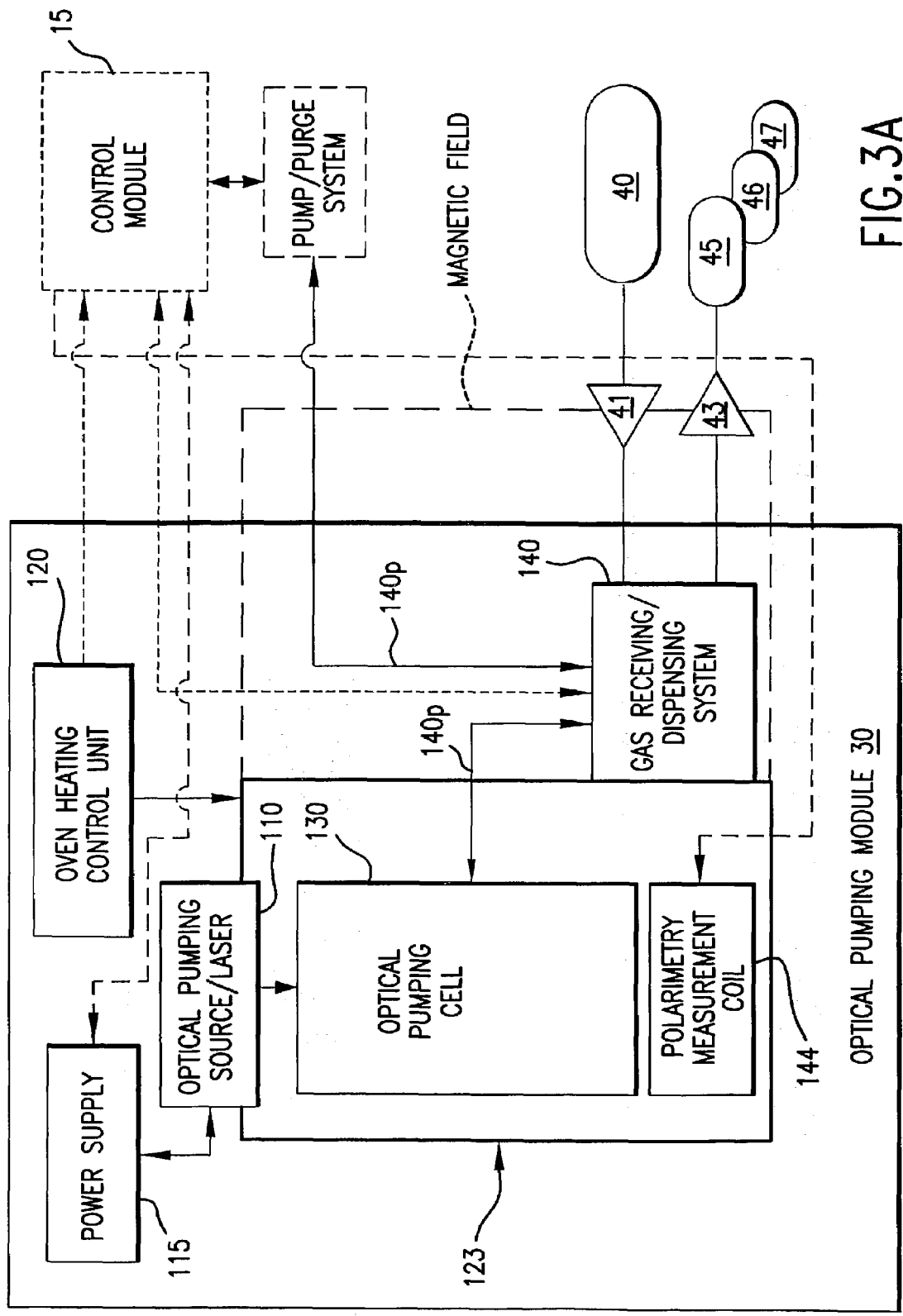
FIG. 3A is a block diagram of an optical pumping module according to embodiments of the present invention.

FIG. 3A illustrates one embodiment of an optical pumping module 30. As shown, the optical pumping module 30 includes a power supply 115, an optical pumping cell 130, an oven 123 configured to encase the optical pumping cell 130, an oven heating control unit 120 (that can include heat sensors and the like which are not shown), an optical pumping source 110 (such as a laser, and in particular embodiments a diode laser array), a polarimetry measurement coil 144, a gas receiving/dispensing system 140, and plumbing 140p (with valves and solenoids or actuators) defining the selectable fluid flow paths for purge gas and polarized gas. The optical module 30 can also include a magnetic field source capable of generating a magnetic field B$_0$ (shown by the dark broken lines that cover a portion of the optical pumping module and extends to cover the gas dispensing port 43). The field B$_0$ may be further generated, formed or shaped to extend to cover the receiving containers of polarized gas 45, 46, 47 during dispensing. The field source may be a pair of Helmholtz coils as is well known to those of skill in the art. In certain embodiments, the field source is a solenoid that is configured to generate the magnetic field. The solenoid can be configured to surround the optical pumping cell. The polarized gas can be dispensed from the optical pumping module by directing the gas to flow or dispense along the axis of the solenoid. Suitable solenoid field sources and configurations are described in co-assigned, co-pending U.S. patent application Ser. No. 09/333,571, the contents of which are hereby incorporated by reference as if recited in full herein.

In other embodiments, the optical modules housing 30h can be configured to generate one or more fields for the optical pumping modules (not shown).

In operation, for each production run on each pumping module, after the control module 15 has directed the evacuation and gas-purging of the optical pumping cell 130 and related plumbing 140p, the pre-packaged container 40 holding the unpolarized gas mixture 40g is opened and the gas directed into the optical pumping module 30 and into the optical pumping cell 130. The container 40 may be a collapsible bag sized so that the pre-packaged amount of unpolarized gas does not completely fill the capacity and, instead, only partially fills the volumetric capacity thereof. For example, filling to about 30-60% capacity may provide a suitable expansion factor. This can allow for expansion of the gas during transport at increased altitudes or other environmental or shipping conditions.

The hyperpolarizer 10 can include one or more purifiers or filters (not shown) can be positioned in line with the plumbing to remove impurities such as water vapor, alkali metal, and oxygen from the system (or to inhibit their entry therein). The hyperpolarizer 10 can also include various sensors including a flow meter as well as a plurality of valves as well as electrical solenoids, hydraulic, or pneumatic actuators that can be controlled by the controller 19 to define the fluid flow path and operation of the components of the hyperpolarizer 10. As will be understood by those of skill in the art, other flow control mechanisms, and devices (analog and electronic) may be used within the scope of the present invention.

Again referring to FIG. 3A, generally stated, the optical pumping source 110 is a light source such as a laser (i.e., a diode laser array) directed into the optical pumping (or polarizer) cell 130 through various focusing and light distributing means, such as lenses, mirrors, and the like (not shown). In certain embodiments, the laser is circularly polarized to optically pump alkali metal held in the cell 130. The cell 130 is positioned inside a temperature-regulated oven 123 (illustrated by a heavy line). The temperature during polarization may be between 170-200° C.

Generally described, the optical pumping modules 30, 31 are configured to polarize noble gas via spin-exchange. The unpolarized pre-packaged gas mixture is introduced into the polarizer optical pumping cell 130. The polarization process can be relatively lengthy, depending on the type of gas and amount of polarized gas desired. For example, a typical $^3$He polarization time of typical single patient dose amounts can be from about 1-6 hours, while $^{129}$Xe may be configured to produce a single patient dose (of about 1 liter)) in about 1-3 hours and typically in about 60-90 minutes or less.

For $^{129}$Xe "continuous" flow based polarization, the typical residence time of the gas in the cell 130 is about 10-30 seconds; i.e., it takes on the order of 10-30 seconds for the gas mixture to be hyperpolarized while moving through the cell 130. The polarizer cell 130 can be a high pressure optical pumping cell. During operation, the oven 123 defines a heated chamber with apertures configured to allow entry of the laser emitted light into the optical pumping cell 130. A vaporized alkali metal such as Rb is introduced into the polarizer cell 130. The Rb vapor is optically pumped via the optic light source.

The optical cell can also employ helium as a buffer gas to pressure broaden the Rb vapor absorption bandwidth. The selection of a buffer gas is important because the buffer gas—while broadening the absorption bandwidth—can also undesirably impact the alkali metal-noble gas spin-exchange by potentially introducing an angular momentum loss of the alkali metal to the buffer gas rather than to the noble gas as desired.

As will be appreciated by those of skill in the art, Rb is reactive with $H_2O$. Therefore, any water or water vapor introduced into the polarizer cell 130 can cause the Rb to lose laser absorption and decrease the amount or efficiency of the spin-exchange in the polarizer cell 130. Thus, as an additional precaution, an extra filter or purifier (not shown) can be positioned before the inlet of the polarizer cell 130 with extra surface area to remove even additional amounts of this undesirable impurity in order to further increase the efficiency of the hyperpolarizer 10.

In any event, once the polarization process is complete, polarized gas exits the optical pumping cell 130, and is ultimately directed to gas dispensing system 140 and then to a collection or accumulation container such as a patient delivery container or drug container (see FIGS. 3A and 45-47 and FIG. 5D).

Figure 3B:
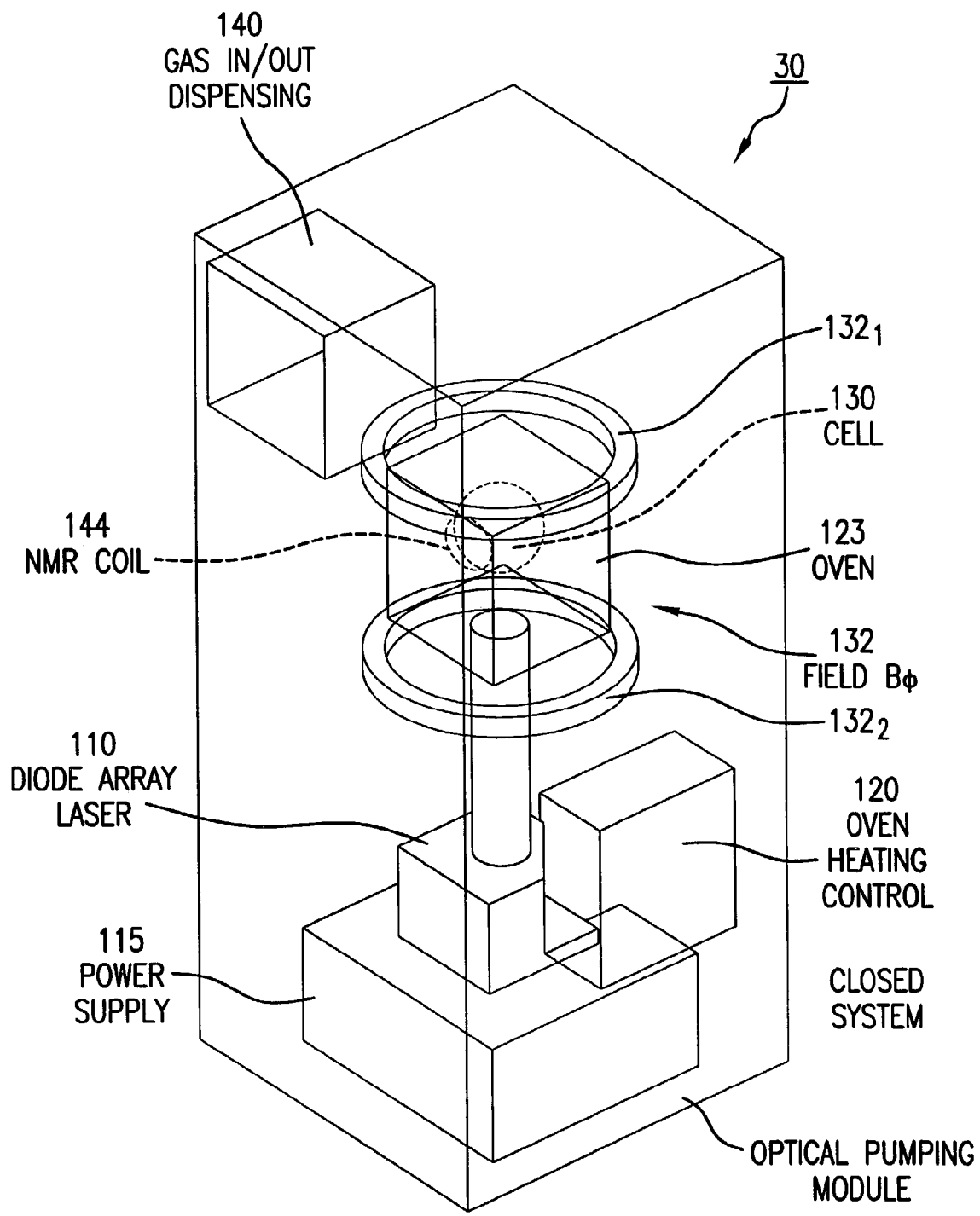
FIG. 3B is a perspective view of a modular optical pumping cell according to embodiments of the present invention.

FIG. 3B illustrates one embodiment of a modular self-contained optical pumping module 30. As shown, certain components are arranged so that they are axially aligned. As shown, the components are serially identified as: the power supply 115; the oven heating control unit 120; the oven 123; and the optical pumping cell 130 therein with the gas in/out dispensing module 140 located so that it is externally accessible. Other portions of the manifold (i.e., the flow path defined by plumbing, valves, and the like), are not shown for ease of illustration. Thus, the laser 110 axially extends such that it is proximate to the oven 123 that holds the optical pumping cell 130 therein. The Helmholtz coil pair $132_1$, $132_2$ are arranged on opposing sides of the oven and optical cell, 123, 130, respectively. As noted above, a solenoid can also be used to provide the magnetic field about the optical cell.

The hyperpolarizer unit 10 can also include a cooling means to cool the optical pumping cell 130 after the polarization process. The cooling means can include a refrigeration source that can turn the oven 123 into a cooling chamber or that can be located along the plumbing or exit flow path (such as in the gas dispensing line) to precipitate the alkali metal from the polarized gas stream. In other embodiments, heat to the oven 123 is turned off and natural cooling is used to condense the Rb out of the vapor phase and collect it in the bottom of the optical pumping cell 130. In addition, a micro-pore filter can be positioned in the gas dispensing line or in the exit flow path (extending between the optical cell exit port to the dispensing port). As will be appreciated by one of skill in the art, the alkali metal can precipitate out of the gas stream at temperatures of about 40° C. Other filtering means can also be used, such as, but not limited to, an alkali metal reflux condenser (not shown). The refluxing condenser employs a vertical refluxing outlet pipe that can be kept at room temperature. The gas flow velocity through the refluxing pipe and the size of the refluxing outlet pipe is such that the alkali metal vapor condenses and drips back into the pumping cell by gravitational force.

Typically, the polarized $^{129}$Xe is then accumulated in a cold finger where it is frozen and subsequently thawed to provide the polarized $^{129}$Xe in the dose mixture. Additional description of suitable polarizers and cold fingers is included in U.S. Pat. Nos. 5,642,625, 5,809,801, and 6,709,213, the contents of which are hereby incorporated by reference as if recited in full herein. In any event, it is desirable to remove alkali metal prior to delivering polarized gas to a patient to provide a non-toxic, sterile, or pharmaceutically acceptable substance (i.e., one that is suitable for in vivo administration).

A delivery or receiving container such as a patient dose bag or other vessel can be attached to the dispensing outlet 43 (FIG. 2). A valve or other device located thereat can be opened to evacuate the attached bag. Once the bag is evacuated, the polarized gas can be directed into the bag directly or into a mixing/blending chamber (not shown) where a high-grade biocompatible filler gas can be added as desired in a desired blend formulation.

In certain embodiments, the blending is performed in situ corresponding to the scheduled procedure (and its associated gas formulation) and/or the polarization level of the gas. That is, the hyperpolarizer 10 can be configured with a mixing/blending chamber and a source of biocompatible fluid that will be combined with the polarized gas to provide the blended formulation of pharmaceutical polarized gas product proximate in time and at the production site of the polarized gas itself.

In other embodiments, the receiving container can be pre-filled with a high purity medical grade holding gas such as $N_2$ to inhibit the permeation of oxygen therein. The holding gas can form part of the blended formulation or can be expelled prior to dispensing the polarized gas or gas mixture.

In certain particular embodiments, after the polarized gas is cooled to about ambient temperature, a polarization measurement is obtained and the formulated blend volume of unpolarized gas added based on the polarization level to form a controlled blend for more consistent imaging/NMR evaluations procedure to procedure. The blending may be carried out automatically by the hyperpolarizer 10 by controlling the amount of polarized gas and the amount of fluid blending constituent(s) that is released into the mixing/blending chamber or released separately into the dispensing container to provide the formulated blend. For additional description of optical pumping modules, systems, and blending methods, see co-assigned and concurrently filed Provisional U.S. Application Serial No., identified by Ser. No. 9036-26PR, the contents of which are hereby incorporated by reference as if recited in full herein. See also, U.S. patent application Ser. No. 09/949,394 for descriptions of methods and devices for providing meted formulations and amounts of polarized gas, the contents of which are hereby incorporated by reference as if recited in full herein.

In certain embodiments, for obtaining polarimetry measurements, the $T_2$* value can be in excess of about 5 ms or more (such as where a solenoid is used to provide the magnetic field). An example of a typical mute time after the pulse is transmitted is about 3 ms. This means that for a hyperpolarizer unit 10 with a magnetic field $B_0$ generated by an optical pumping module with an integrated "on-board" 6-19 inch diameter Helmholtz coils, the coils are positioned and configured to generate a region of homogeneity which is defined by a virtual cylinder having a length of less than about 2 inches and a radius of less than about 2 inches centered between the coils. In other embodiments employing solenoid magnetic field sources, an end compensated solenoid (to flatten out and extend the homogeneous field as described in U.S. patent application Ser. No. 09/333,571 referenced hereinabove) that can be sized and configured with about a 10-12 inch diameter. The solenoid may also be configured to be about 20-60 inches long or even longer, and typically can be about 40 inches long.

Figure 4A:
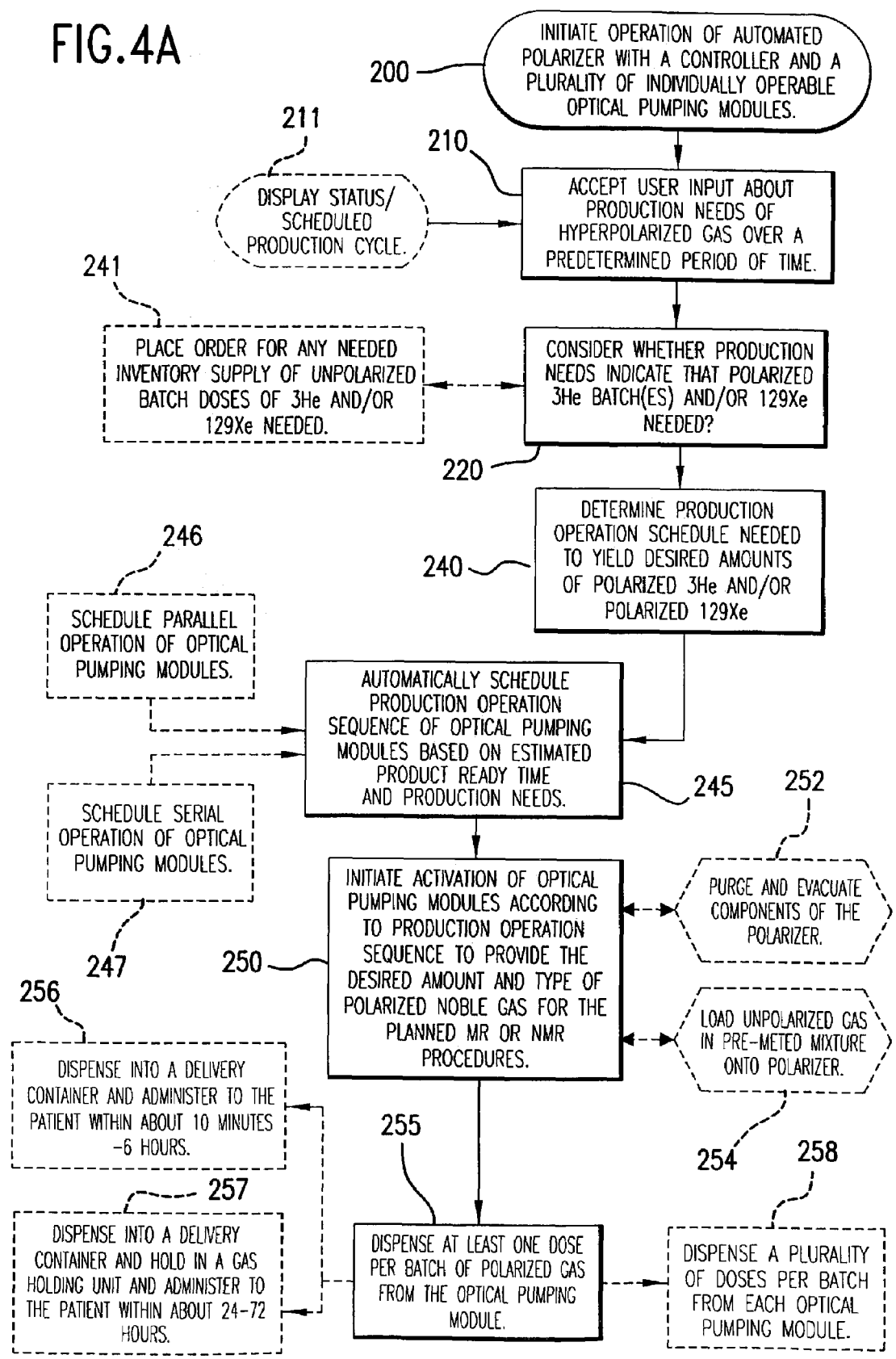
FIG. 4A is flow diagram of operations of a hyperpolarizer according to embodiments of the present invention.

FIG. 4A illustrates examples of operations according to embodiments of the present invention. As shown, operation of an automated hyperpolarizer having a central controller and a plurality of optical pumping modules can be initiated (block 200). The hyperpolarizer can accept user input regarding the number of procedures, the type of procedure scheduled and the days and times of the scheduled appointments over a selected period of time (block 210). The user input may indicate whether the planned procedure is for NMR or MRI evaluation (or both). For example, the scheduled procedure can be correlated to the quantity and type of polarized gas or gas formulation that is needed to support the procedure. This may include one or both injected or inhaled formulations and quantities, and the amount may depend on whether the procedure will be for ventilation (typically static), dynamic imaging or signal analysis, oxygen diffusion/perfusion mapping, dynamic with oxygen mapping or perfusion. The procedure can also indicate what is the targeted region to be evaluated, such as, but not limited to, the pulmonary system, the cardio-pulmonary system, the cerebrum or brain, or another other organ, system, or region of interest. Information regarding the scheduled procedure can be used to generate an estimated associated polarized gas amount and type needed to support the planned evaluation.

In certain embodiments, the system can display the operational status and production cycle and/or schedule that is planned for the hyperpolarizer (block 211). This information can also be monitored remotely via a computer or wireless link (to the facility or clinic or a remote service station). Thus, when there is a discrepancy between production capacity and need, an alert can be generated so that remedial steps can be taken in advance of the appointment of the patient to avoid NMR/MRI system downtime. This can be to reschedule the patient, obtain additional supplies of polarized gas from a different source, and the like.

The production data can be reviewed to determine whether one or both polarized $^3$He and $^{129}$Xe are needed (block 220). The system can also be configured to track an inventory supply of unpolarized production run or batch amounts of $^3$He and $^{129}$Xe that may be needed to support the production schedule and indicate that orders for additional amounts are needed (and when) (block 241). The batch amounts of $^3$He and $^{129}$Xe can be supplied as pre-mixed and pre-packaged formulations of blends to provide single production run blends in convenient production kits (that can have a shelf life of up to about 6 months) and indicate whether and when additional batch kits are needed.

The system can be configured to project or forecast a production schedule and need requirement that can be periodically re-evaluated (such as daily or even more often). The production operation schedule can be determined that can provide the desired amounts of polarized $^3$He and/or $^{129}$Xe (block 240). That is, the time it takes to produce a batch of the desired type of polarized gas is estimated and the time that the doses are required are known as well as the life expectation limits of same. The system can be configured to compute one or more production schedules to meet the production demand and the life expectancy of the polarized gas.

In addition, a reserve supply of polarized gas can be generated for each 12 hour period; however, it is anticipated that this amount will be limited to control costs as the product if unused within a reasonable time will be wasted. In addition, if the reserve is depleted, the immediate or current day supply production run period (0-12 hours) and a subsequent period can be revised to allow for a reserve supply to be generated. In other embodiments, the production schedule is re-evaluated every 6-48 hour period, so that the production run schedule yields the desired amount of polarized gas for the next 24-48 hours, 24-72 hours, or other time interval period. For example, if there are no procedures planned for Day 0, the current day, four MRI procedures planned for Day 1, and 5 MRI procedures planned for Day 2, and the production capacity is 3 production runs per day (per 8-12 hour period), then either the polarizer can run at full capacity on Day 0 and a second shift can be scheduled to run the hyperpolarizer on either Day 1 or Day 2. Of course, other adjustments can also yield the desired production volumes.

The hyperpolarizer can be operated to automatically schedule the production operation sequence of the optical pumping modules based on estimated product ready time (per batch) and the production need (patient delivery/appointment time) (block 245). The optical pumping modules can be scheduled to operate in parallel (block 246) or in series (block 247). That is, the optical pumping modules can have staggered start times with overlapping periods of operation or operate serially one after the other is completed. Activation of the optical pumping modules can be initiated according to the production operation sequence schedule to provide the desired amount and type of polarized gas for the planned MRI or NMR procedure (block 250). The system can purge and evacuate certain components of the polarizer (block 252) prior to initiate of the polarization. In addition, the unpolarized gas mixture (in a meted pre-packaged amount) can be loaded into the optical pumping module (block 254).

At least one dose of polarized gas per production run or batch can be dispensed from the optical pumping module (block 255). In certain embodiments, a plurality of doses per batch can be dispensed from each optical pumping module (block 258). The dose can be dispensed into a delivery container and administered to the patient within about 10 minutes to 6 hours (block 256). In other embodiments, the dose can be dispensed into a patient delivery receptacle or container and held in a gas holding chamber or unit to be subsequently administered to the patient within about 24-72 hours from dispensing (block 257). The container can include a label with the polarization measurement and time taken or with a projected shelf-life use time.

Thus, the polarization can be carried out in a "just-in-time" format, or so that limited storage (typically within about 24-72 hours of dispensing) of the polarized gas is required. Longer storage times can be used in certain applications. However, both polarized $^{129}$Xe and $^3$He have a limited clinically useful polarization life. The polarization life depends on a number of factors, including surface-induced relaxation mechanism. For example, the collisions of gaseous $^{129}$Xe and $^3$He with container walls ("surface relaxation") have historically been thought to dominate most relaxation processes. Another relaxation mechanism is the relaxation due to EMI and oscillating magnetic fields. Unfortunately, EMI can be generated by relatively common sources; as such, transport away from the hyperpolarized gas production site can expose the hyperpolarized gas to these undesirable relaxation sources which, in turn, can dramatically reduce the polarization life of the transported gas (i.e., the $T_1$). For example, EMI is typically generated from a vehicle's engine, high voltage lines, power stations and other current carrying entities. Still another relaxation mechanism is magnetic gradient relaxation that involves the relaxation attributed to the exposure of the hyperpolarized noble gases to inhomogeneous static magnetic fields. Generally stated, as the polarized gas atoms diffuse or move through an inhomogeneous magnetic field, they experience a time-dependent field, which can introduce depolarizing activity onto the hyperpolarized atoms. See U.S. Pat. No. 6,269,648 for additional description of relaxation mechanisms and for a description of shielded transport and storage containers or chambers, the contents of which are hereby incorporated by reference as if recited in full herein.

Figure 4B:
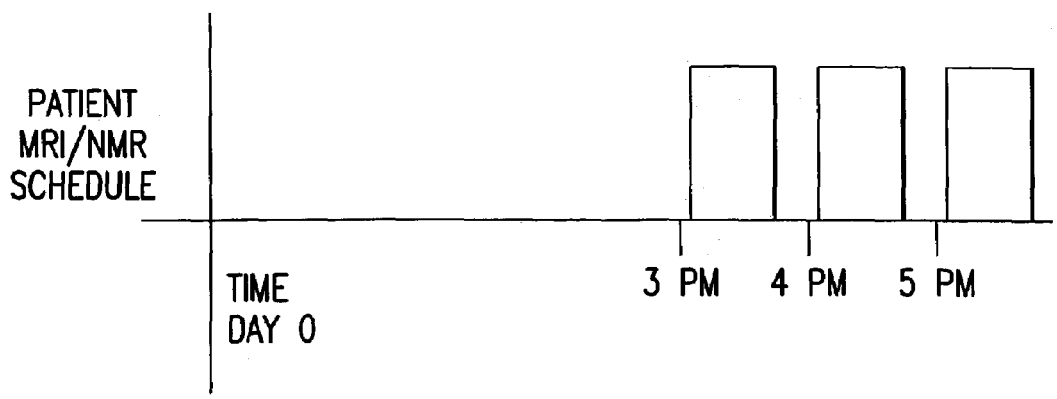
FIG. 4B is a timing graph of patient procedures and FIGS. 4C and 4D are examples of corresponding schedules of production runs of optical modules according to embodiments of the present invention.
Figure 4C:
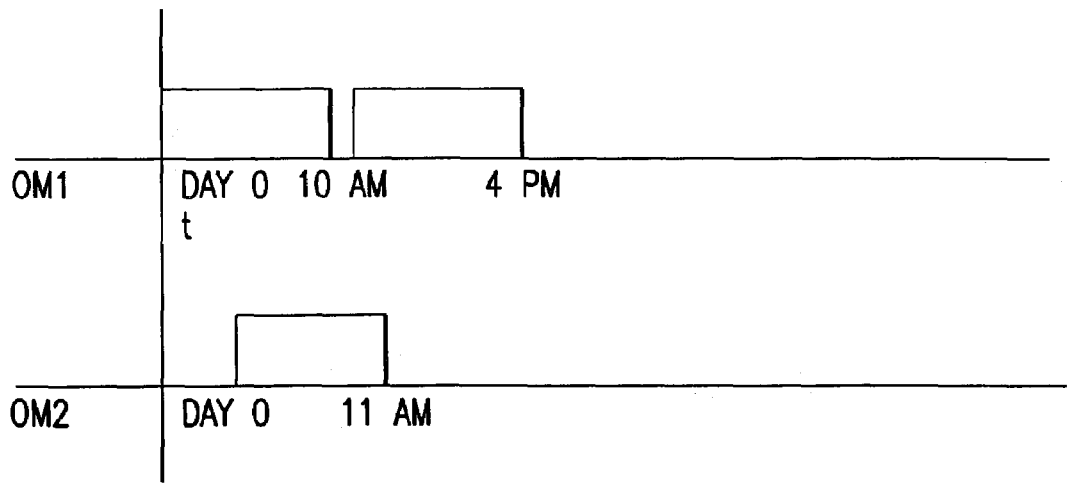

FIG. 4B illustrates the MRI/NMR equipment schedule for patient evaluations using polarized gas. As shown, the procedures may be clustered together to reduce any equipment set-up adjustments needed to run the polarized gas evaluations. Thus, in this example, there are three different procedures scheduled, one each at 3 pm, 4 pm, and 5 pm. FIG. 4C illustrates the production sequence for the optical modules 1 (OM1) and 2 (OM2) that may be used to provide the polarized gas. As shown, OM1 provides two batches of polarized gas, one being ready at 10 am and the other at 4 pm. OM2 provides one batch, available at 11 am.

Figure 4D:
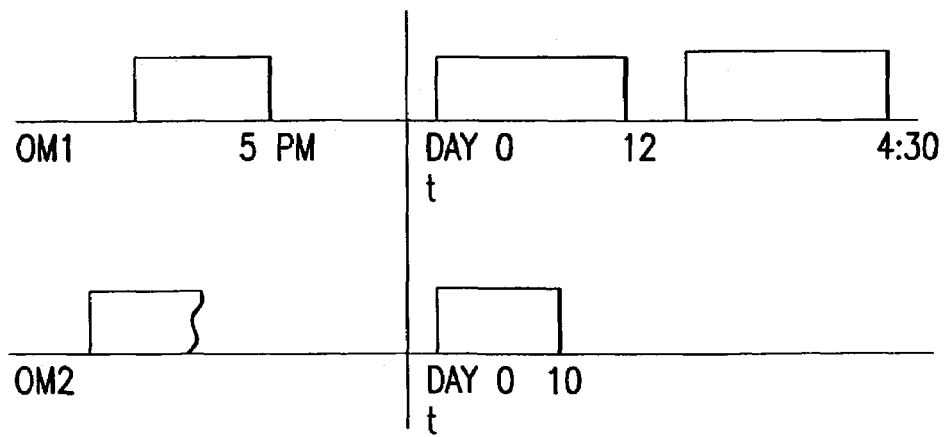

FIG. 4D illustrates another potential schedule sequence. That is, OM1 produces one batch of polarized gas the day before the planned use day (shown as ready at 5 pm). OM2 is shown as also imitating a polarization the previous days, but the procedure having shut down prematurely. Then on Day 0, the day of the planned procedures, OM1 produces two additional batches while OM2 again is running and produces one batch.

FIG. 5 illustrates one potential distribution system according to an embodiment of the present invention. As shown in FIG. 5A, one or more hyperpolarizers 10 can be located at a central or regional polarization facility (or on a transportable based system such as a truck or bus mobile unit) and polarized gas can be dispensed into a gas container (not shown), which is then held in a shielded gas transport unit 245. The gas container can be formed as a cavity in the gas transport unit 245 or can be a separate container. The sequence of operations is indicated by the direction of the arrows in the figures.

As shown in FIG. 5B, the gas transport unit 245 shields the gas during transport from the central or regional facility and delivers the polarized gas to the hospital or clinical site in the vicinity of the MRI or equipment suite. FIG. 5C illustrates that the gas transport unit 245 (with the polarized gas held therein) can be placed in a gas holding or storage chamber 249. The gas transport container 245 and/or the gas holding chamber 249 can be configured to obtain polarimetry measurements to ascertain the polarization level of the gas.

As shown, the gas transport container can include a polarized gas release port 245$p$ that aligns with the holding chamber gas release port 249$p$ so that the polarized gas can be released in situ through both devices into a patient delivery container 145 (shown as a collapsible bag). The delivery bag is then filled (FIG. 5D) and used to administer the polarized gas to the subject during the procedure (FIG. 5E). The delivery bag can then be disposed (single-use disposable container)(FIG. 5F1) and the gas transport container returned to be used again (FIG. 5F2).

FIG. 6 illustrates another embodiment of a distribution system according to the present invention. As shown in FIG. 6A, in this embodiment, one or more central or regional unpolarized gas filling facilities can be used to produce pre-packaged gas into a container 40 in blended or meted amounts of the target noble gas to be polarized and other constituents in the desired production formulation suitable for polarization in the optical pumping modules. The container 40 can be configured to hold the gas under increased pressure (to be able to expel the gas as an aerosol) or to hold the high-purity gas mixture in an unpressurized state. In certain embodiments, the container is configured so that provides an unpolarized gas shelf life of between about 1-6 months. As shown by FIG. 6C, the hyperpolarizer 10 can be located at the point of use site (hospital or clinic) typically in the vicinity of or proximate to the MRI or NMR equipment. That is, the hyperpolarizer 10 can reside adjacent the MRI suite or in a room of a wing proximate thereto so as to limit the spatial transport and potential exposure to undesirable environmental conditions. In certain embodiments, the polarized gas transport time between the hyperpolarizer and the imaging suite is less than about 1 hour. Placing the hyperpolarizer in the clinic or hospital allows for short and consistent transport times procedure to procedure. In addition, formulating the pharmaceutical polarized gas with a polarized gas having higher levels of polarization can reduce the amount of the polarized gas used to form the end dose product thereby potentially reducing the cost of the product.

As indicated by the broken lines around the pre-packaged container 40 of unpolarized gas mixture 40$g$ and the patient delivery device 145, the two components can be shipped as a part of a production batch kit 313 that includes one or more patient delivery containers with the unpolarized gas mixture. The patient delivery container 145 can be shipped partially filled with a biocompatible fluid such as nitrogen. After polarization, the polarized gas is dispensed into the patient delivery container 145 and then either directly administered to the patient (FIG. 6E) or held in a gas holding chamber 249' that can be configured to obtain polarimetry measurements (FIG. 6D). As such, the gas holding chamber can operate as a type of "calibration" station. Prior to use, the polarization reading of the gas can be obtained and this information used to calibrate the signal strength of the NMR data of the polarized gas in the patient during the evaluation session. The container 145 may be configured with an integrated NMR excitation coil and lead wire that can be engaged with the gas holding chamber polarimetry system (not shown). Again, the containers from the kit 313 can be discarded after a single use.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A hyperpolarizer for producing polarized noble gases, comprising:
    a control module configured to direct the operation of a hyperpolarizer;
    a first optical pumping module operably associated with the control module;
    a second optical pumping module operably associated with the control module; and
    a scheduling sequencer unit comprising program code for accepting user input regarding polarized gas requirements and program code for automatically scheduling the operation of at least one of the first and second optical pumping modules based on the polarized gas requirements.

2. A hyperpolarizer according to claim 1, wherein the first and second optical pumping modules are configured, during operation, to be in concurrent communication with the control module so that the control module can direct the first and second optical pumping modules to commence operation either serially so that the start times are sequentially staggered in time, or in parallel so that the operate concurrently for at least a portion of the time.

3. A hyperpolarizer according to claim 1, further comprising a third optical pumping module operably associated with the control module.

4. A hyperpolarizer according to claim 1, wherein the first and second optical pumping modules are configured to polarize $^3$He.

5. A hyperpolarizer according to claim 1, wherein the first and second optical pumping modules are configured to polarize $^{129}$Xe.

6. A hyperpolarizer according to claim 1, wherein the first optical pumping module is configured to polarize $^3$He and the second optical pumping module is configured to polarize $^{129}$Xe.

7. A hyperpolarizer according to claim 1, wherein the control module comprises:
    a power supply;
    a source of high purity medical grade purge gas;
    a vacuum pump; and
    a fluid distribution manifold with control means to selectively direct purge gas and air to and from the optical pumping modules.

8. A hyperpolarizer according to claim 7, wherein the fluid distribution manifold comprises plumbing and a plurality of valves and solenoids configured to cooperate upon commands sent from the control module to direct purge gas to or from the optical pumping module.

9. A hyperpolarizer according to claim 1, wherein each of the first and second optical pumping modules comprise:
    an optical pumping cell having a non-polarized gas inlet port and a polarized gas outlet port, the optical pumping cell sized and configured to produce polarized gas in a batch quantity sufficient to supply at least one patient procedure;
    an oven configured to enclose the optical pumping cell therein;
    an oven heating control unit;
    a magnetic field source configured to generate a magnetic field that covers at least a portion of the optical pumping cell;
    a laser operably associated with the optical pumping cell;
    an NMR coil located proximate the optical pumping cell; and
    a power supply,
wherein the first and second optical pumping modules are configured to engage with the control module so as to be in electrical and fluid communication therewith.

10. A hyperpolarizer according to claim 9, wherein the optical pumping modules are each configured in a self-contained replaceable housing unit.

11. A hyperpolarizer according to claim 10, wherein the optical pumping modules are each configured as a substantially rectangular case.

12. A hyperpolarizer according to claim 1, wherein the control module comprises a housing with upstanding walls configured to engage with and hold a plurality of optical pumping cells vertically stacked and substantially aligned therein.

13. A hyperpolarizer according to claim 1, wherein the first and second optical pumping modules further comprise an optical pumping cell configured to polarize inert noble gas via spin-exchange with an alkali metal, the optical pumping cell being in fluid communication with a gas distribution and dispensing system, wherein during operation, a pre-determined batch quantity of non-polarized inert gas mixture is directed into the gas distribution system and into the optical pumping cell.

14. A hyperpolarizer according to claim 1, wherein the first optical pumping module comprises:
    an optical pumping cell configured to hold the inert gas therein during the spin exchange to generate the polarized gas; and
    an NMR coil positioned proximate the optical pumping cell in communication with the control module, and wherein, during operation, the control module monitors the level of polarization of the noble gas, and wherein when the monitored level of polarization departs from a predetermined level or other operational problem is detected, an error message is generated and the second optical pumping module activated.

15. A hyperpolarizer comprising a control module and a plurality of expansion slots, each expansion slot configured to engage the control module with an optical pumping module, wherein the hyperpolarizer can operate both with one optical pumping module and a plurality of optical pumping modules depending on a production site's capacity requirements.

16. A method of operating a hyperpolarizer having a plurality of optical pumping cells, comprising:
    identifying the polarized gas requirements for a selected time period based on patient scheduling; and
    automatically determining a production operation sequence schedule of the hyperpolarizer so as to identify start times of each of the plurality of optical pumping cells and a number of batches to be produced by each of the optical pumping cells so as to be able to produce polarized gas in a sufficient quantity to meet the identified polarized gas requirements.

17. A method according to claim 16, further comprising automatically commencing the operation of the optical pumping cells at the determined times.

18. A computer program product for operating a hyperpolarizer having at least one optical pumping cell to produce polarized noble gas, the computer program product comprising:
- a computer readable storage medium having computer readable program code embodied in said medium, said computer-readable program code comprising:
- computer readable program code that determines the desired production goals over a selected time;
- computer readable program code that schedules the sequence of activation and start times of the polarization process in the optical pumping cells; and
- computer readable program code that automatically initiates the operation of at least one of the optical pumping cells according to the scheduled sequence.

19. A computer program product according to claim 18, further comprising computer program code that accepts user input regarding patient scheduled appointments where polarized gas is needed, wherein the computer readable program code that schedules the sequence of activation and start times of the polarization process in the optical pumping cells considers the patient schedule demands for polarized gas.

20. A computer program product according to claim 19, further comprising computer program code that identifies the type of NMR or MRI procedure is scheduled for the patients and determines the type and amount of polarized gas corresponding thereto, and wherein the computer readable program code that schedules the sequence of activation and start times of the polarization process in the optical pumping cells considers the type of procedure and/or type of polarized gas needed for the scheduled patient evaluations or appointments.

* * * * *